(12) United States Patent
Chen et al.

(10) Patent No.: US 7,066,190 B2
(45) Date of Patent: Jun. 27, 2006

(54) AIR-DRIVEN MICROFLUID CONTROL DEVICE AND METHOD

(75) Inventors: Chien-An Chen, Hsinchu (TW); Shun-Chieh Yang, Taipei Hsien (TW)

(73) Assignee: Dr. Chip Biotechnology Incorporation, Miaoli (TW)

( * ) Notice: Subject to any disclaimer, the term of this patent is extended or adjusted under 35 U.S.C. 154(b) by 532 days.

(21) Appl. No.: 10/618,999

(22) Filed: Jul. 15, 2003

(65) Prior Publication Data

US 2004/0216790 A1  Nov. 4, 2004

(30) Foreign Application Priority Data

Apr. 29, 2003 (TW) ................. 92110026 A

(51) Int. Cl.
*F17D 3/00* (2006.01)
*F15C 1/18* (2006.01)

(52) U.S. Cl. .................. 137/12; 137/14; 137/806; 137/842; 204/600

(58) Field of Classification Search .............. 137/14, 137/806; 422/100; 204/601, 600
See application file for complete search history.

(56) References Cited

U.S. PATENT DOCUMENTS

| 5,304,487 A | * | 4/1994 | Wilding et al. | ................ 435/29 |
| 5,632,876 A | * | 5/1997 | Zanzucchi et al. | .......... 204/600 |
| 6,192,939 B1 | | 2/2001 | Yao et al. | |
| 6,450,189 B1 | * | 9/2002 | Ganan-Calvo | ................ 137/12 |

* cited by examiner

*Primary Examiner*—A. Michael Chambers
(74) *Attorney, Agent, or Firm*—Rabin & Berdo, P.C.

(57) ABSTRACT

An air-driven microfluid control device and its method are disclosed. The control device contains an air source, a first inlet, a second inlet, a narrow sector, and an outlet. The air source is connected two the two inlets to produce an airflow. The first inlet connects to the narrow sector, which then connects to the outlet. The air flows through the first inlet and the narrow sector and exits via the outlet. A fluid tunnel connects to the narrows sideways. The second inlet connects to the fluid tunnel so that the air entering the second inlet flows into the fluid tunnel. Through the interaction between the two inlets, pushing and pulling forces can be produced to control the fluid inside the fluid tunnel.

18 Claims, 4 Drawing Sheets

AIR-DRIVEN MICROFLUID CONTROL DEVICE AND METHOD

BACKGROUND OF THE INVENTION

1. Field of Invention

The invention relates to a microfluid control device and the method. In particular, the invention relates to an air-driven microfluid control device and its method that use an external air source as the fluid power source.

2. Related Art

With the development in biotechnology, various biochips analyses utilizing proteins and DNA's are getting popular. The biochip takes very few specimens and test agents and has them undergo a series of fluid processing steps for the biochemical materials in the chip to fully mix with the test agents for reactions. Since the whole process happens on a tiny chip, how to control and transport fluid inside the chip becomes relatively important. Some microfluidic driving devices are thus invented, having the functions of controlling fluid transportation and preventing specimen and test agents from polluting each other. To satisfy the medical and biochemical testing requirements, disposable biochips with low costs and easy to control are important subjects under study.

At the current stage, the methods of driving fluid on chips can be divided into two types: the built-in-chip type and the external server driving type. The built-in-chip type includes mechanical micropumps and non-mechanical micropumps. The mechanical micropumps are comprised of pumps, actuators, and stop valves. Since the complicated microstructure of this type of mobile devices is manufactured using micro electro-mechanical system (MEMS) processes, the costs are relatively higher.

The non-mechanical micropump has different constraints for different designs. According to the driving methods, there are thermal-bubble, electrohydrodynamic, electro-osmosis, and electrophoretic micropumps. The thermal-bubble ones require appropriate tunnels designs. The electrohydrodynamic, electro-osmosis, and electrophoretic ones are limited in its driving range. The volume flow rate is smaller than 100 µl/min ($10^{-6}$ L/min). One also has to impose a high voltage within a short distance. Generally speaking, the structure and control method of built-in-chip microfluid driving devices are complicated and expensive. They are thus unsuitable for disposable chips.

In comparison, the external server driving system moves the power for driving microfluid outside the chip, using a non-contact method to drive the fluid inside the chip. Therefore, the chip structure can be simplified and the cost also gets lower. The currently developed air-driven fluid driving system uses the on/off combination of five air valves to generate the pushing and pulling forces, thereby controlling the fluid inside the chip. For details, please refer to the U.S. Pat. No. 6,192,939. Nonetheless, the method involving the on/off combination of five air valves is too complicated. Such complications also increase the cost of the whole system.

SUMMARY OF THE INVENTION

To solve the problems in the prior art, the invention provides an air-driven microfluid control device and the method. The control device is connected to the fluid tunnel of the fluid chip to control the push and pull of fluid inside the tunnel.

The control device contains an air source, a first inlet, a second inlet, a narrow sector, and an outlet. The air source is connected to the two inlets to produce airflow. The first inlet connects to the narrow sector, which then connects to the outlet. A fluid tunnel connects the narrow sector sideways. The air flows through the first inlet and the narrow sector and exits via the outlet. The second inlet connects to the fluid tunnel so that the air entering the second inlet flows into the fluid tunnel to produce a pushing force.

When the air-driven microfluid control device wants to produce a pulling force in the fluid tunnel, air flows through the first inlet and the second inlet is closed. According to the Bernoulli's law, when a fluid flows through a pipe the flow speed is smaller (larger) and the pressure is larger (smaller) at the place with a larger (smaller) cross section. When the air from the first inlet flows through the narrow sector, a negative pressure region with a pressure smaller than the external pressure is generated. This produces a pulling force in the fluid tunnel to pull the fluid into the fluid tunnel. On the other hand, to generate a pushing force, air flows through the second inlet and the first inlet is closed. Therefore, the air entering the second inlet directly flows into the fluid tunnel, producing a positive pressure greater than the atmospheric pressure. Therefore, a pushing force is generated to push a fluid inside the fluid tunnel.

The invention further provides an air-driven microfluid control method for pushing and pulling fluid inside the fluid tunnel. The steps involved in the method are as follows. First, provide a first airflow channel, which contains a first inlet, a narrow sector, and an outlet. The first inlet connects to the narrow sector, which then connects to the outlet. A fluid tunnel connects to the side of the narrow sector. Secondly, provide a second airflow channel, which contains a second inlet connecting to the fluid tunnel so that the air flows through the second inlet into the fluid tunnel. Thirdly, provide an air source, which connects to the first inlet and the second inlet to provide air. Supply air to the first inlet to generate a first airflow and lock the second inlet. When the first airflow goes through the narrow sector, a negative pressure is produced so that a pulling force is formed to drive the fluid into the fluid tunnel. Supply air to the second inlet to produce a second airflow and lock the first inlet. The second airflow goes directly into the fluid tunnel, producing a positive pressure to push a fluid inside the fluid tunnel forward.

The two airflow channels of the air-driven microfluid control device can be installed with the fluid tunnel on the same fluid chip to drive the fluid inside the fluid tunnel. The first airflow channel and the second airflow channel of the fluid chip connect to the air source. By switching the inlets of the two airflow channels, pulling and pushing forces are produced to control the motion of the fluid inside the fluid tunnel. The first airflow channel includes a first inlet, a narrow sector, and an outlet. The diameter of the first inlet gradually shrinks toward the narrow sector, which then connects to the outlet. The fluid tunnel and the second inlet of the second airflow channel are connected via the first airflow channel. Therefore, the air from the second inlet can enter the fluid tunnel.

The disclosed air-driven microfluid control device only requires the use of a simple air control system in order to control the motion of the fluid. The needed airflow rate is smaller. This can effectively reduce the cost of biochemical experiments. Therefore, the invention only needs to use airflow to drive the fluid without pollution in between.

BRIEF DESCRIPTION OF THE DRAWINGS

The invention will become more fully understood from the detailed description given hereinbelow illustration only, and thus are not limitative of the present invention, and wherein.

DETAILED DESCRIPTION OF THE INVENTION

The air-driven microfluid control device of the invention contains an air source connecting to two airflow channels to generate airflows. The airflow channels are connected to a fluid tunnel. With different airflows, the fluid can be driven to go forward, to go backward, and to stop. This achieves the goal of controlling the fluid motion.

Figure 1:
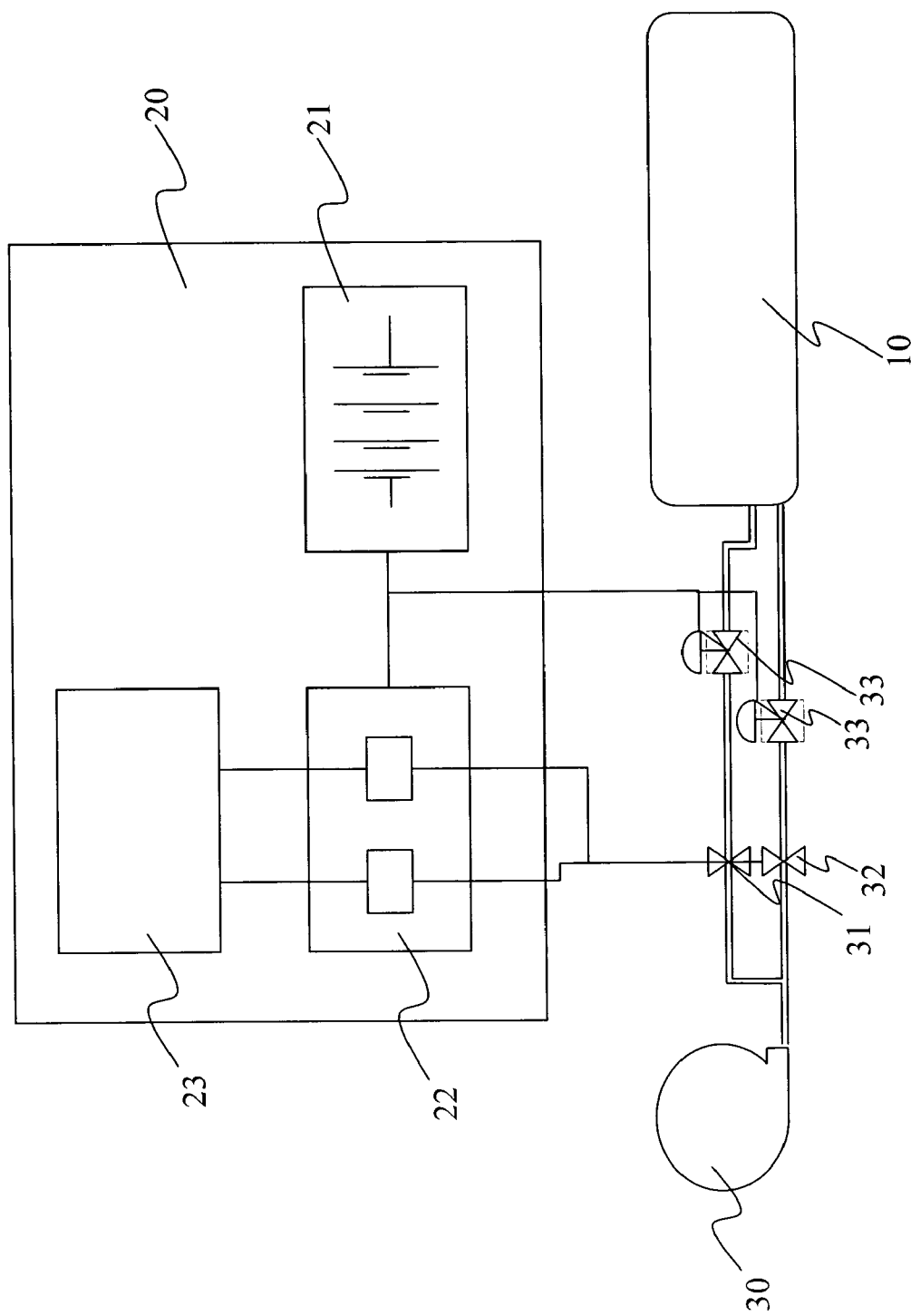
FIG. 1 is a schematic view of the disclosed system in the first embodiment.

With reference to FIG. 1, a control system 20 and a fluid chip 10 are combined to control the fluid inside the fluid chip according to the first embodiment of the invention. The external air source is an air compressor 30 that generates compressed air and sends the airflow into the fluid chip. The control system 20 includes an electronic signal control interface 23, a relay 22, and a power supply 21. Furthermore, a first inlet valve 31, a second inlet valve 32, and a pressure adjuster 33 are used to control the rate of airflow into the fluid chip 10.

Figure 2:
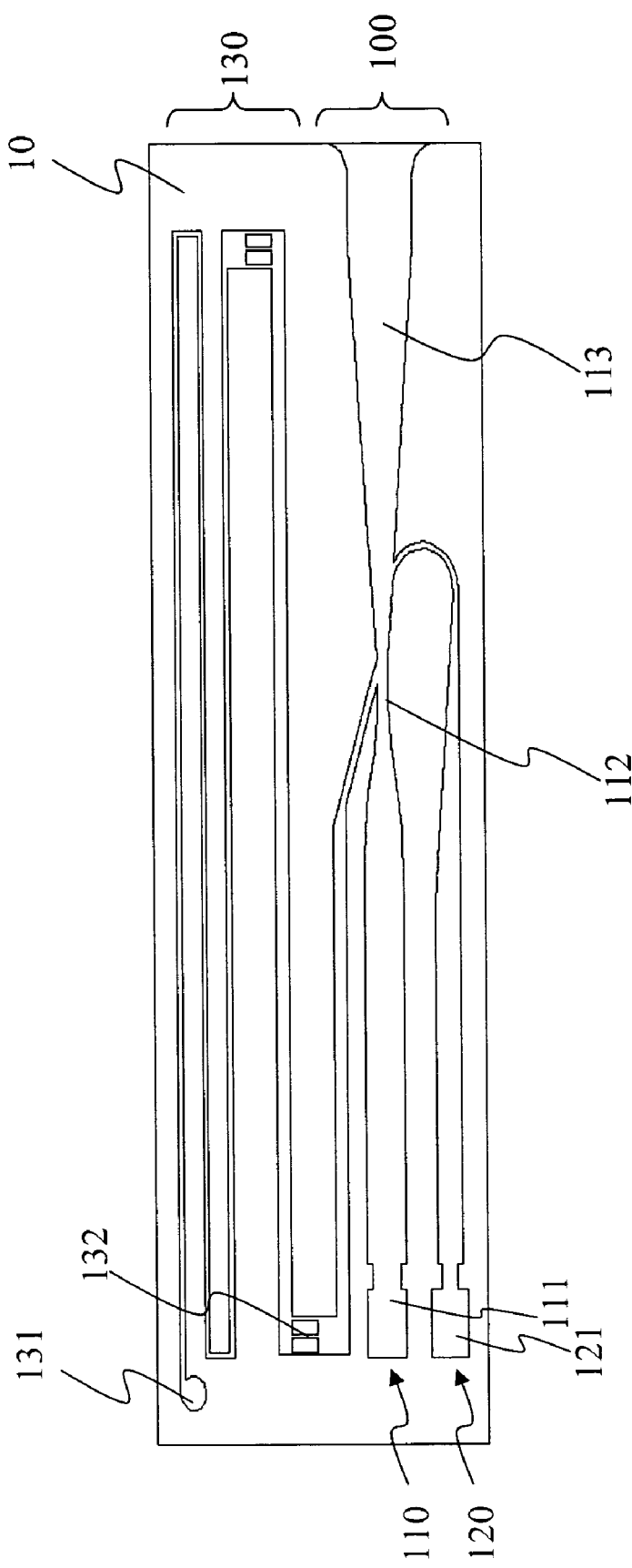
FIG. 2 is a schematic view of the fluid chip structure in the first embodiment.

With reference to FIG. 2, the first embodiment fluid chip contains a fluid reservoir 131, a reaction region 132, a fluid tunnel 130, and an air-driven microfluid control device 100. The fluid reservoir 131 is installed at the beginning of the fluid tunnel 130 and stores a test fluid. The air-driven microfluid control device 100 connects to the end of the fluid tunnel 130. It produces a dragging force on the test fluid to flow through the fluid tunnel 130, reaching the reaction region 132. After reactions in the reaction region, the fluid is pushed by the air-driven microfluid control device 100 away from the reaction region 132. The reaction region 132 contains a huge amount of bio-molecules on a reaction surface for having specific reactions with the test fluid.

The disclosed air-driven microfluid control method utilizes the interactions between two airflow channels to produce pulling and pushing forces on a fluid. As shown in FIG. 2, the first airflow channel 110 and the second airflow channel 120 connect to the air source. The airflow rate into the airflow tunnel is controlled by the first inlet valve 31 and the second inlet valve 32. The interactions of the airflow between the first airflow channel 110 and the second airflow channel 120 produce pulling and pushing forces to drive the fluid inside the fluid tunnel 130. The first airflow channel 110 contains a first inlet 111, a narrow sector 112, and an outlet 113. The diameter of the inlet 111 gradually shrinks into the narrow sector 112, which then connects to the outlet 113. The fluid tunnel connects to the narrow sector 112 from the side. The second airflow channel 120 is curved. The second inlet 121 of the second airflow channel is in fluid communications with the fluid tunnel 130 via the first airflow channel 110. Therefore, the airflow provided from the second inlet 121 enters the fluid tunnel 130 via the first airflow channel 110.

When having biochemical reactions, a test agent is placed in the fluid reservoir 131. The pulling mode has the first inlet valve 31 open while the second inlet valve 32 closed. When the airflow passes the narrow sector 112, a negative pressure region with a pressure less than the atmospheric pressure is produced because of the Bernoulli's effect. A pulling force is thus generated to pull the test agent in the fluid reservoir 131 into the reaction region 132 in the fluid tunnel 130. On the other hand, the pushing mode has the second valve 32 open while the first inlet valve 31 closed. The narrow sector 112 of the airflow channel has a positive pressure that is greater than the atmospheric pressure. A pushing force is generated to push the test agent away from the reaction region 132.

Figure 3:
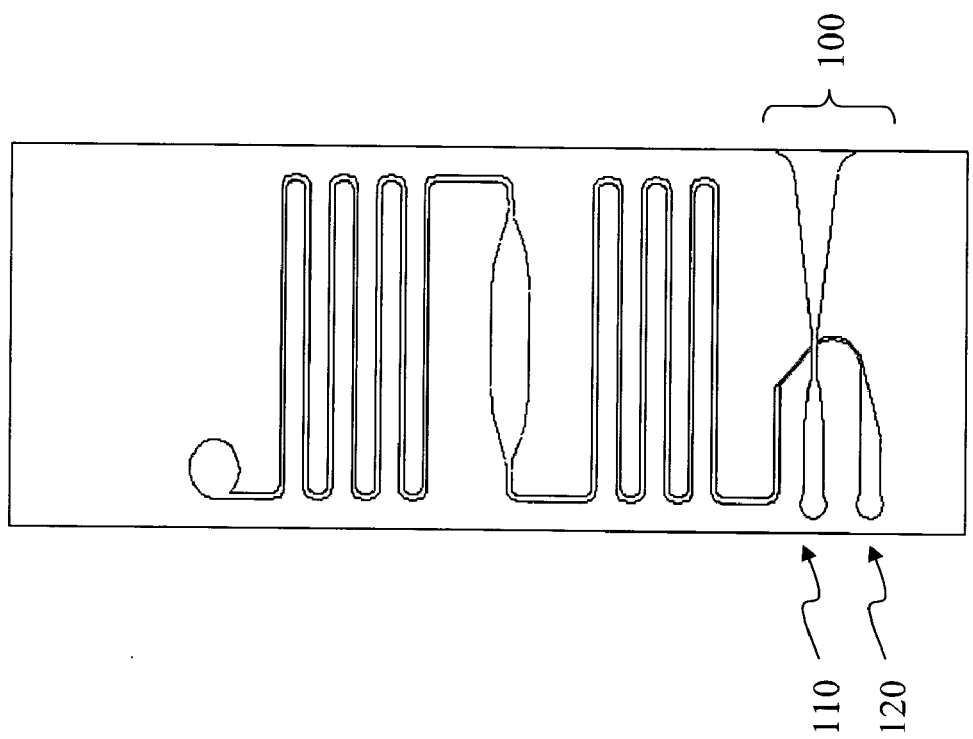
FIG. 3 is a schematic view of the fluid chip structure in the second embodiment.

The disclosed air-driven microfluid control device only uses the interactions between two airflow channels to produce pulling and pushing forces. As it has a simple structure that can be accommodated into any type of fluid chips, it helps simplifying the chip design and size. FIG. 3 shows another fluid chip structure. The airflow direction of its first airflow channel 110 and second airflow channel 120 is parallel to the wider side of the fluid chip, occupying an even smaller area of the fluid chip. Therefore, a larger test area can be provided.

Figure 4:
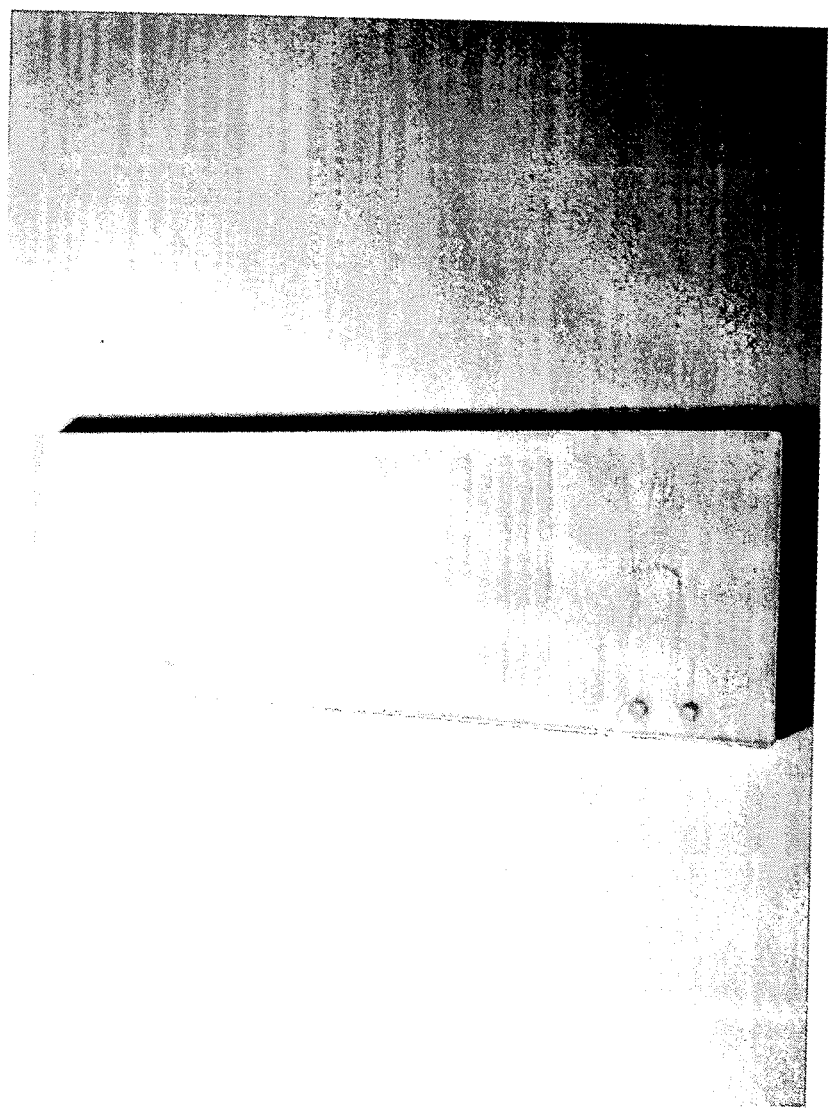
FIG. 4 is a diagram of a fluid chip in a second embodiment of the invention.

The structure design of the air-driven microfluid control device is relatively simple. In an embodiment of the invention, the material of the fluid chip can be a normal polymer, such as polymethyl methacrylate (PMMA), polystyrene (PS), polycarbonate (PC), and polypropylene (PP). Please refer to FIG. 4, which is a diagram of a fluid chip in a second embodiment of the invention. Its material is PMMA, has a size of 76 mm a 26 mm, and is covered with a transparent top cover.

In comparison with the prior art, the disclosed air-driven microfluid control device can provide a larger volume flow rate. Moreover, the fluid flow rate inside the fluid tunnel can be controlled by the airflow speed of the air source. The fluid volume in the second embodiment is about 150 µl ($150 \times 10^{-6}$ liters). The volume of the reaction region is about 15 µl. The air intake flow rate of the inlet valve is about 7 ml/s. Using water as the driving fluid, the fluid flow rates in the pulling mode and the pushing mode are listed in Table 1.

TABLE 1

|  | Air Flow Rate (ml/s) | Fluid Flow Rate (µl/s) |
| --- | --- | --- |
| Pushing Mode | 7 | 5.8 |
| Pulling Mode | 7 | 7 |

From Table 1, we see that its fluid flow rate is greater than the prior art.

The invention can use the airflow speed of the air source to control the fluid flow rate inside the fluid tunnel. Using water as the driving fluid, the fluid flow rate in the pulling mode is listed in Table 2.

TABLE 2

| Airflow Speed (m/s) | Fluid Flow Rate (µl/s) |
| --- | --- |
| 3 | 1.2 |
| 5 | 2.3 |
| 7 | 2.8 |
| 13.3 | 5.32 |

According to Table 2, the larger the airflow speed at the inlet is, the more the negative pressure in the narrow sector is and so is the generated pulling force. The invention can use a simple control system to control the airflow speed so that the fluid flow rate can be controlled more accurately and easily.

Certain variations would be apparent to those skilled in the art, which variations are considered within the spirit and scope of the claimed invention.

What is claimed is:

1. An air-driven microfluid control device, which is applied for pulling and pushing a fluid inside a fluid tunnel, comprising:
   an air source, which provides an airflow;
   a first inlet, which connects to the air source for guiding the airflow;
   a narrow sector, which connects to the first inlet and connects from its side to the fluid tunnel;
   an outlet, which connects to the narrow sector so that the airflow from the first inlet goes through the narrow sector and leaves via the outlet; and
   a second inlet, which connects to the fluid tunnel so that the airflow from the second inlet enters the fluid tunnel to generate a pushing force;
   wherein a negative pressure lower than the external pressure is produced in the narrow sector to pull the fluid into the fluid tunnel when the first inlet provides an airflow while the second inlet is closed, and a positive pressure greater than the external pressure is produced in the narrow sector to push the fluid away from the fluid tunnel when the first inlet is closed while the second inlet provides an airflow.

2. The air-driven microfluid control device of claim 1, wherein the second inlet is a curved airflow channel.

3. The air-driven microfluid control device of claim 1, wherein the air source is an air compressor.

4. The air-driven microfluid control device of claim 1, wherein the second inlet connects to the narrow sector and is in fluid communications with the fluid tunnel.

5. The air-driven microfluid control device of claim 1 further comprising a control system to control the airflow from the air source into the first inlet and the second inlet.

6. The air-driven microfluid control device of claim 5, wherein the control system includes a pressure adjuster and an electronic signal control interface.

7. An air-driven microfluid control method, which is applied for pulling and pushing a fluid inside a fluid tunnel, comprising the steps of:
   providing a first airflow channel, which includes a first inlet, a narrow sector, and an outlet, wherein the first inlet connects to the narrow sector, the narrow sector then connects to the outlet, and the fluid tunnel connects to the narrow sector from its side;
   providing a second airflow channel, which includes a second inlet connecting to the fluid tunnel for the airflow from the second inlet to enter the fluid tunnel;
   providing an air source, which connects to the first inlet and the second inlet for providing air;
   providing air at the first inlet to generate a first airflow and closing the second inlet, the first airflow producing a negative pressure smaller than the external pressure when passing through the narrow sector, pulling the fluid into the fluid tunnel; and
   providing air at the second inlet to generate a second airflow and closing the first inlet, the second airflow producing a positive pressure greater than the external pressure when passing through the narrow sector, pushing the fluid away from the fluid tunnel.

8. The method of claim 7, wherein the second inlet is a curved airflow channel.

9. The method of claim 7, wherein the air source is an air compressor.

10. The method of claim 7, wherein the second inlet connects to the narrow sector and is in fluid communications with the fluid tunnel.

11. The method of claim 7 further comprising a control system to control the airflow from the air source into the first inlet and the second inlet.

12. The method of claim 11, wherein the control system includes a pressure adjuster and an electronic signal control interface.

13. An air-driven microfluid control device, which connects to a fluid tunnel of a fluid chip for pulling and pushing a fluid inside the fluid tunnel, comprising:
    a first airflow channel, which includes a first inlet, a narrow sector, and an outlet, wherein the first inlet has a diameter gradually shrinking to that of the narrow sector and connects to the narrow sector, the narrow sector then connects to the outlet, the fluid tunnel connects to the narrow sector from its side, and the airflow from the first inlet goes through the narrow sector and leaves via the outlet;
    a second airflow channel, which includes a second inlet, wherein the second airflow channel is in communications with the fluid tunnel via the first airflow channel for the airflow from the second inlet to enter the fluid tunnel; and
    an air source, which connects to the first inlet and the second inlet, respectively, for providing airflows;
    wherein a negative pressure lower than the external pressure is produced in the narrow sector to pull the fluid into the fluid tunnel when the first inlet provides an airflow while the second inlet is closed, and a positive pressure greater than the external pressure is produced in the narrow sector to push the fluid away from the fluid tunnel when the first inlet is closed while the second inlet provides an airflow.

14. The air-driven microfluid control device of claim 13, wherein the second inlet is a curved airflow channel.

15. The air-driven microfluid control device of claim 13, wherein the air source is an air compressor.

16. The air-driven microfluid control device of claim 13, wherein the second inlet connects to the narrow sector and is in fluid communications with the fluid tunnel.

17. The air-driven microfluid control device of claim 13 further comprising a control system to control the airflow from the air source into the first inlet and the second inlet.

18. The air-driven microfluid control device of claim 17, wherein the control system includes a pressure adjuster and an electronic signal control interface.

* * * * *